United States Patent
Uzunian et al.

(12) 
(10) Patent No.: US 6,627,212 B2
(45) Date of Patent: Sep. 30, 2003

(54) USE OF EFFECT PIGMENTS IN INGESTED DRUGS

(75) Inventors: Gabriel E. Uzunian, Rye, NY (US); William Joseph Sullivan, Ossining, NY (US)

(73) Assignee: Engelhard Corporation, Iselin, NJ (US)

( * ) Notice: Subject to any disclaimer, the term of this patent is extended or adjusted under 35 U.S.C. 154(b) by 0 days.

(21) Appl. No.: 09/891,725

(22) Filed: Jun. 26, 2001

(65) Prior Publication Data

US 2003/0008002 A1 Jan. 9, 2003

(51) Int. Cl.[7] .......................... A61K 47/00; A23L 1/216
(52) U.S. Cl. ...................... 424/439; 424/490; 426/96
(58) Field of Search ............................... 106/415, 430; 424/490, 400, 439; 426/96

(56) References Cited

U.S. PATENT DOCUMENTS

| | | |
|---|---|---|
| 3,138,475 A | 6/1964 | Schroder et al. |
| 3,340,006 A | 9/1967 | Mochel |
| 3,395,203 A | 7/1968 | Morita |
| 3,582,382 A | 6/1971 | Watanabe et al. |
| 3,658,552 A | 4/1972 | Carlson et al. |
| 4,001,390 A * | 1/1977 | Ohno et al. .................... 424/35 |
| 4,996,067 A | 2/1991 | Kobayashi et al. |
| 5,149,369 A | 9/1992 | Eberts et al. |
| 5,244,669 A | 9/1993 | Satoh et al. |
| 5,433,956 A | 7/1995 | Patel |
| 5,541,231 A | 7/1996 | Ruff et al. |
| 5,562,763 A * | 10/1996 | Bruckner et al. ............ 106/403 |
| 5,811,082 A * | 9/1998 | Ahlnäs et al. ................. 424/59 |
| 5,858,078 A | 1/1999 | Andes et al. |

FOREIGN PATENT DOCUMENTS

| | | | |
|---|---|---|---|
| EP | 0649816 A1 | 4/1995 | |
| GB | 2257433 A | 1/1993 | |
| WO | WO 00/03609 * | 1/2000 | ........... A23L/1/275 |

OTHER PUBLICATIONS

Abstract (DialogIP); JP 6126820 A; Matsumoto Yushi Seiyaku KK; Granular drug composition ofr animals—obtained by spraying dispersion of crytllising substance in fused mixture of drug and wax; May 22 1985.*

Copy of International Search Report dated Nov. 12, 2002.

Abstract (esp@cenet); DE4214367; Gerhard, et al.; Colour pigment particle for use with foodstuff—comprises aluminum body with overcoat film of ferric oxide; published Nov. 11, 1993.

Patent Abstracts of Japan; 07223816; Yukie, et al.; Photochromic Composite Material, Production Thereof and External Agent for Skin; published Aug. 22, 1995.

Abstract (Derwent/WPI); JP1264932A; Ishihara Sangyo Kaisha Ltd.; Manufacture Acicular Titanium Dioxide Pigment React Acid Alkali Tin Salt Aqueous Titanium Dioxide Slurry Effect Surface Coating; Oct. 23, 1989.

Abstract (DialogIP); JP 61268620 A; Matsumoto Yushi Seiyaku KK; Granular drug composition for animals—obtained by spraying dispersion of crystallising substance in fused mixture of drug and wax; May 22, 1985.

* cited by examiner

*Primary Examiner*—Carlos Azpuru
*Assistant Examiner*—Micah Paul Young

(57) ABSTRACT

Ingestible drugs contain an effect pigment.

17 Claims, No Drawings

USE OF EFFECT PIGMENTS IN INGESTED DRUGS

BACKGROUND OF THE INVENTION

This invention relates to the use of effect pigments including platy titanium dioxide pigments, titanium dioxide and/or iron oxide coated on inorganic platy substrates, and combinations of the same, in ingestible drugs including pharmaceuticals and related oral products. These pigments provides a unique optical effect in such ingested drugs. They can also be used in decorative applications for foods (e.g. in cake frostings, gelatin desserts and candy coatings) and drugs, as well as for functional uses, such as a unique way to mark/identify drugs. Such effects are not possible using conventional absorption colorants.

SUMMARY OF THE INVENTION

This invention relates to the use of effect pigments including pearlescent pigments and platy titanium dioxide pigments in ingestible and oral drug products. The resulting compositions are also a part of this invention.

DESCRIPTION OF THE INVENTION

As used in this specification, the term "ingestible" product means a product which is intended in the ordinary course of use to be swallowed, for instance, a foodstuff or beverage or an orally administered pharmaceutical composition. The type of ingestible product or oral composition is not restricted. The ingestible product or oral composition is preferably intended for human use. As used in this specification, the term "drug" means a therapeutic agent, i.e., any substance, other than food, used in the prevention, diagnosis, alleviation, treatment or cure of disease in man and animals. The term thus encompasses, for example, both pharmaceuticals and vitamins and the like products.

Effect pigments per se are well known. These pigments are usually a laminar materials with relatively high indexes of refraction relative to the medium in which they are incorporated. As a result of the reflection and refraction of light, these pigments can exhibit pearl-like luster, and interference color and/or color travel. The effect pigments most often encountered commercially are those which are coating on a support, and particularly are titanium dioxide coated and iron oxide coated micas. One of the effect (pearlescent) pigments used in the present invention is the well-known titanium coated mica. The particle size of such pigments is preferably about 200 $\mu$m or less and more preferably about 100 $\mu$m or less.

Platy $TiO_2$ pigments, i.e., titanium dioxide platelets which exhibit interference colors but are not deposited on a substrate, per se are known. These pigments have a laminar structure and are distinct from pearlescent pigments which, as just noted, are based on coating a support. By the term "platy" is meant the pigment particles have an aspect ratio of at least about 2 to 1 and a largest dimension of about 1 to 150 $\mu$m, and more preferably about 3 to 75 $\mu$m. Therefore, a platy $TiO_2$ interference pigment is defined as consisting of smooth platelets of $TiO_2$ having a high aspect ratio and controlled thickness such that various interference colors are produced depending on the thickness of the platelet.

A number of other platy effect pigments are covered by this invention. They include, but are not restricted to, platy iron oxide pigments, platy bismuth oxychloride pigments, platy guanine pigments, platy aluminum oxide, platy silicon dioxide, platey pigments of the genreal formula $Mn_xAl_yFe_{2-(x+y)}O_3$, platy metal flake pigments such as aluminum, and any combinations of these. The combinations may be blends of the various pigments, or depositions of one or more on another of these. For example, a platy iron oxide pigment may be used to create a unique optical effect in a coating. Alternately, iron oxide may be coated on a platy titanium dioxide substratum, achieving a distinctly different effect.

The effect pigments can be combined with natural colorants, color pigments or coloring fruit and plant extracts to give the food or pharmaceutical an interesting new shade. Examples of fruit and plant extracts that could be used as a colorant include carrot juice, red beet juice, elder juice, hibiscus juice, paprika extract and aronia extract. The effect pigment of the invention can add increased light and moisture protection to the colored food or pharmaceutical. Vitamin preparations, for example, can be stored for a longer period of time. Also in some cases, such as colored tablets, a delayed release of the active ingredients can be established or augmented.

The pigment is incorporated into the ingestible product or oral composition in any convenient manner. The pigment may be incorporated in a coating system, or alternately, in the composition itself. The amount is not restricted and any amount which provides the desired optical effect can be employed. In general, the total concentration of all coloring agents in the food or pharmaceutical should not exceed about 12% by weight, although it can go up to about 15% by weight. Some products can be colored with as low as about 0.005% by weight. Preferably, the amount of effect pigment is about 0.01 to 6% by weight, and more preferably, about 0.1 to 2% by weight. Where combined with another colorant, the mixture ratio of the effect pigment with the other colorant depends upon the desired effect and is preferably about 20:1 to 1:20 and more preferably about 5:1 to 1:1. A surprising and unexpected aspect of the present invention, and one unique to the platy $TiO_2$ pigment is that very low concentrations can be employed while achieving the desired effect. An amount which is one-half or less of the amount of non-platy titanium dioxide-coated mica pigments can be used to achieve the same effect. Typically, a concentration of about 1 weight % or less can be employed.

Coatings on all types of food can be colored with the agent of the present invention. Examples include pigmented sugar in shellac coatings, both alcoholic and aqueous, coatings of oils and waxes in combination with gum arabic and with cellulose material such as hydroxypropylmethyl cellulose, cake decorations, compressed products, dragees, chewing gum, gum products, fondant products, marzipan, fillings, cocoa gum, glazes, chocolate containing products, ice cream, cereal, snacks, produce, cake bases, gel and gelatin products, candy, licorice, puddings, desserts, icings, beverages, milk products and the like. Colored tablets, gelatin capsules, coated tablets, ointments and syrups are other products of the present invention.

In order to illustrate the invention, various examples are set forth below. It will be appreciated, however, that these are intended to be illustrative and are not intended to be limiting.

EXAMPLE 1

A mixture was prepared by combining 88.05 grams of gelatin powder with 0.10 grams of platy gold titanium dioxide with an average particle size of 6 microns. Three quarters of a cup of boiling water was added to the mixture with stirring and the stirring was continued until the mixture had become completely dissolved. A one-half cup of cold water and ice cubes sufficient to form one and one-quarter cups of material were added and stirring was continued until the product was slightly thickened. Thereafter, the product was placed into the refrigerator. The resulting gelatin product had a unique gold pearlescent appearance.

EXAMPLE 2

Example 1 was repeated except that the mixture contained 85.92 grams of cranberry flavored gelatin powder and 0.34 gram of the colorant.

EXAMPLE 3

Example 1 was repeated except that the mixture contained 85.92 grams of strawberry flavored gelatin powder and 0.34 gram of the colorant.

EXAMPLE 4

A coating mixture was prepared by combining 10 grams of #1 pure refined powdered carnauba wax and 0.1 gram of platy $TiO_2$ pigment. The blend was used to coat M&M brand chocolate candies. The resulting candies had a lustrous gold exterior appearance.

EXAMPLE 5

A blend was prepared with 20 grams of #1 pure refined powdered carnauba wax and 3 grams of platy gold titanium dioxide with an average particle size of 6 microns and used to coat EXCEDRIN® extra strength tablets. The tablets had a gold highlight over a blue background.

EXAMPLE

Ten grams of platy gold titanium dioxide with an average particle size of 6 microns was combined with 150 grams of isopropyl alcohol and the resulting dispersion was used to coat Alka Seltzer Plus brand cold medicine tablets.

EXAMPLE 7

5.45 grams of platy gold titanium dioxide with an average particle size of 6 microns was combined with 0.10 gram of xanthan gum and 99.9 grams of water. The resulting solution was used to coat SKITTLES® brand chocolate candies.

EXAMPLE 8

A mixture is prepared by combining 88.05 grams of gelatin powder with 0.10 grams of Flamenco® Gold—a titanium dioxide coated mica gold interference pigment. Three quarters of a cup of boiling water is added to the mixture with stirring and the stirring is continued until the mixture had become completely dissolved. A one-half cup of cold water and ice cubes sufficient to form one and one-quarter cups of material are added and stirring continued until the product is slightly thickened. Thereafter, the product is placed into the refrigerator. A unique gold pearlescent appearance is achieved.

EXAMPLE 9

Example 8 is repeated, except that the pigment is replaced with Cloisonne® Gold—an iron oxide and titanium dioxide coated mica effect pigment.

EXAMPLE 10

Example 5 is repeated, except the mixture contained PearlGlo UVR®, a platy bismuth oxychloride effect pigment.

EXAMPLE 11

Example 5 is repeated, except the mixture contained Mearlmaid® AA, a dispersion of platy guanine effect pigment.

EXAMPLE 12

Example 5 is repeated, except the mixture contained a platy iron oxide effect pigment.

EXAMPLE 13

A blend is prepared with 20 grams of #1 pure refined powdered carnauba wax and 3 grams of Flamenco® Gold—a titanium dioxide coated mica gold interference pigment and is used to coat EXCEDRIN® extra strength tablets. This achieves tablets having a gold highlight over a blue background.

EXAMPLE 14

A coating mixture is prepared by combining 10 grams of #1 pure refined powdered carnauba wax and 0.1 gram of Cloisonne® Golden Bronze—an iron oxide coated mica pearlescent pigment. The blend is used to coat M&M brand chocolate candies to obtain a lustrous bronze exterior appearance.

EXAMPLE 15

To obtain candies had a light pink pearlescent exterior appearance, Example 11 is repeated using 0.1 grams of Cloisonne® Red—a carmine coated titanium dioxide coated mica pearlescent pigment as the colorant.

EXAMPLE 16

A pharmaceutical powder was prepared by blending the following proportions of ingredients:

| | |
|---|---|
| Acetaminophen powder, USP | 83.3% |
| Lactose regular grind, NF | 6.1% |
| Calcium sulfate, NF | 6.1% |
| Magnesium stearate, NF | 2.5% |
| Platy gold titanium dioxide | 2.0% |

The resulting mixture was compressed into tablets having a light gold hue.

Although the invention has been described with regard to particular embodiments thereof, other variations and modifications will become apparent to those of ordinary skill in the art from the foregoing disclosure. The present invention is thus not limited to the specific disclosure herein.

What is claimed is:

1. A composition comprising an ingestible drug in admixture with or coated with a platy effect pigment, wherein the platy effect pigment is a platy titanium dioxide pigment, platy iron oxide pigment, platy bismuth oxychloride pigment, platy guanine pigment, or a combination thereof.

2. A composition according to claim 1 wherein the amount of platy effect pigment is about 1 weight percent or less of the composition.

3. A composition according to claim 2 wherein the ingestible drug is a pharmaceutical.

4. A composition according to claim 2 wherein the ingestible drug is a vitamin.

5. A composition according to claim 2 wherein the pigment is in a coating on the surface of the ingestible drug.

6. A composition according to claim 3 wherein the pigment is in admixture with the ingestible drug.

7. A composition according to claim 2 wherein the pigment is platy titanium dioxide.

8. A composition according to claim 1 wherein the ingestible drug is a pharmaceutical.

9. A composition according to claim 1 wherein the ingestible drug is a vitamin.

10. A composition according to claim 1 wherein the pigment is in a coating on the surface of the ingestible drug.

11. A composition according to claim 1 wherein the pigment is in admixture with the ingestible drug.

12. A composition according to claim 1 wherein the pigment is platy titanium dioxide.

13. A composition according to claim 12 wherein the ingestible drug is a pharmaceutical.

14. A composition according to claim 12 wherein the ingestible drug is a vitamin.

15. A composition according to claim 2 wherein the pigment is platy iron oxide.

16. A composition according to claim 2 wherein the pigment is platy bismuth oxychloride.

17. A composition according to claim 2 wherein the pigment is platy guanine.

* * * * *